United States Patent [19]
Olig

[11] Patent Number: 5,902,301
[45] Date of Patent: May 11, 1999

[54] CUTTING/COAGULATING FORCEPS WITH INTERLEAVED ELECTRODES

[75] Inventor: Christopher P. Olig, Edina, Minn.

[73] Assignee: Everest Medical Corporation, Minneapolis, Minn.

[21] Appl. No.: 09/028,039

[22] Filed: Feb. 23, 1998

[51] Int. Cl.⁶ .................................................. A61B 17/39
[52] U.S. Cl. .............................................. 606/48; 606/51
[58] Field of Search ............................ 606/41, 45, 48–52, 606/205–208

[56] References Cited

U.S. PATENT DOCUMENTS

| | | |
|---|---|---|
| 2,068,721 | 1/1937 | Wappler et al. . |
| 2,691,370 | 10/1954 | Wallace . |
| 5,217,460 | 6/1993 | Knoepfler . |
| 5,258,006 | 11/1993 | Rydell et al. . |
| 5,373,854 | 12/1994 | Kolozsi . |
| 5,458,598 | 10/1995 | Feinberg et al. . |
| 5,755,717 | 5/1998 | Yates et al. ................................ 606/51 |

*Primary Examiner*—John P. Leubecker
*Assistant Examiner*—Roy Gibson
*Attorney, Agent, or Firm*—Nikolai, Mersereau & Dietz, P.A.

[57] ABSTRACT

A cutting coagulating bipolar electrosurgical forceps having a pair of jaws that can be moved from an opened to a closed disposition on tissue when grasping and coagulating. The jaws include a plurality of notched or opposed side edges thereof which define a plurality of tabs. The tabs on the first jaw member are offset relative to those of the second jaw member so that when the jaws are made to close, the tabs on the first jaw fall into the notches on the second jaw with the free ends of the tabs on corresponding side edges of each jaw member disposed collinearly relative to one another, but without making electrical contact between the pair of jaws.

15 Claims, 5 Drawing Sheets

CUTTING/COAGULATING FORCEPS WITH INTERLEAVED ELECTRODES

BACKGROUND OF THE INVENTION

I. Field of the Invention

This invention relates generally to electrosurgical instruments for grasping, coagulating and cutting tissue, and more particularly to an electrode configuration for a bipolar cutting/coagulating forceps that is designed to reduce tissue drag on the electrodes during cutting procedures.

II. Discussion of the Prior Art

A variety of electrosurgical instruments have been devised for carrying out various surgical procedures in which tissue needs to be cut and bleeding stemmed. Such electrosurgical devices typically include at least one conductive electrode. Radio frequency energy is conducted through this electrode to either a remote conductive body-plate (monopolar electrosurgery) or to a second, closely-space conductive electrode (bipolar). Current passing through the gap between the two electrodes will coagulate blood and other body fluids placed between those two electrodes.

Monopolar electrosurgical instruments suffer from the fact that the return path between the active electrode and the large area body-plate can be unpredictable as the electrical current seeks the return electrode through a path of least resistance. With bipolar electrosurgical instruments, however, because the two electrodes are closely spaced to one another, usually at the distal end of an instrument handle, the return path is very short and involves the tissue and fluids in the short path between the two electrodes.

In carrying out a surgical procedure, either open or endoscopic, a need often exists for an instrument that can readily cut through tissue and which can also be used to coagulate cut, bleeding blood vessels to promote hemostasis. It is desirable that these features be incorporated into a single instrument so that frequent instrument exchanges by the surgeon become unnecessary.

The Rydell et al. U.S. Pat. No. 5,514,134 describes a bipolar scissors designed for endoscopic use. This instrument mechanically cuts through tissue but includes bipolar electrodes for effecting coagulation. It includes a pair of blades that must be repeatedly opened and closed relative to one another as tissue is being cut in a scissors like action.

The Rydell U.S. Pat. No. 5,462,546 describes a hand-operable forceps instrument having two interfacing pivotal jaw members, each of which is an electrode. The jaw members can be made to meet to produce a pinching or gripping action on tissue and when the electrodes are energized, current is delivered through the jaws to the tissue to effect cauterization. That device, however, does not effectively cut tissue.

U.S. Pat. No. 5,342,381 to Tidemand describes an electrosurgical instrument that can be made to function both as a forceps for grasping and as a scissors for cutting. Again, cutting is only affected by manipulating a scissors handle to cause the blades to open and close in scissors-like fashion.

A need exists for a forceps-type instrument that can be used not only to grasp tissue but which embodies a feature whereby cutting can be achieved by drawing an edge of the instrument across tissue in scalpel-like fashion rather than snipping. While a monopolar instrument for cutting and grasping can readily be implemented, a problem arises when attempting to electrosurgically cut through tissue with a scalpel-like action using bipolar electrodes. For example, if the jaws of a forceps like that shown in the Rydell U.S. Pat. No. 5,258,006 were to be used to effect bipolar cutting, the jaws would have to be held slightly opened with respect to one another as the voltage is applied there across. As the slightly opened jaws are drawn across tissue, only one of the two jaws will be an active electrode, with the other serving as the indifferent or return electrode. Those skilled in the art appreciate that cutting only occurs at the active electrode and as the instrument is drawn across tissue to be cut, the inactive or indifferent electrode drags, making a smooth even cut more difficult. The present invention overcomes this problem.

SUMMARY OF THE INVENTION

The present invention provides an improved electrode structure for a bipolar electrosurgical forceps for use in open surgery or in endoscopic surgery. Because of the electrode configuration, it can readily be used to grasp tissue and to coagulate that grasped tissue when energized. Furthermore, the electrode configuration lends itself to electrosurgical cutting as a scalpel rather than as a scissors and eliminates the drag between the return electrode and tissue being cut.

In accordance with the present invention the pair of jaws of the forceps each comprise a thin, conductive metal sheet having first and second side edges and being folded or otherwise formed at a predetermined, generally obtuse angle along a longitudinal axis that extends between the first and second side edges of the sheet. The side edges of the first and second sheets have a plurality of spaced apart, inwardly extending notches defining a plurality of space-apart tabs. The pair of jaws are supported by the forceps handle structure such that when the pair of jaws are made to close relative to one another, the plurality of tabs on the side edges on one of the pair of jaws fit into the notches on the side edges of the other of the pair of jaws without the jaws electrically contacting one another and with the exposed end edges of the tabs on the first of the pair of the jaws being generally colinear with the exposed end edges of the tabs on the side edges of the second of the pair of jaws. With the exposed end edges colinear, it matters not which of the two jaws happens to be the active or return electrode at any given time in that the return electrode always tracks the path being cut by the active electrode.

DESCRIPTION OF THE DRAWINGS

Further features, objects and advantages will become apparent to those skilled in the art from the following detailed description of a preferred embodiment, especially when considered in conjunction with the accompanying drawings in which like numerals in the several views referred to corresponding parts.

DESCRIPTION OF THE PREFERRED EMBODIMENT

Figure 1:
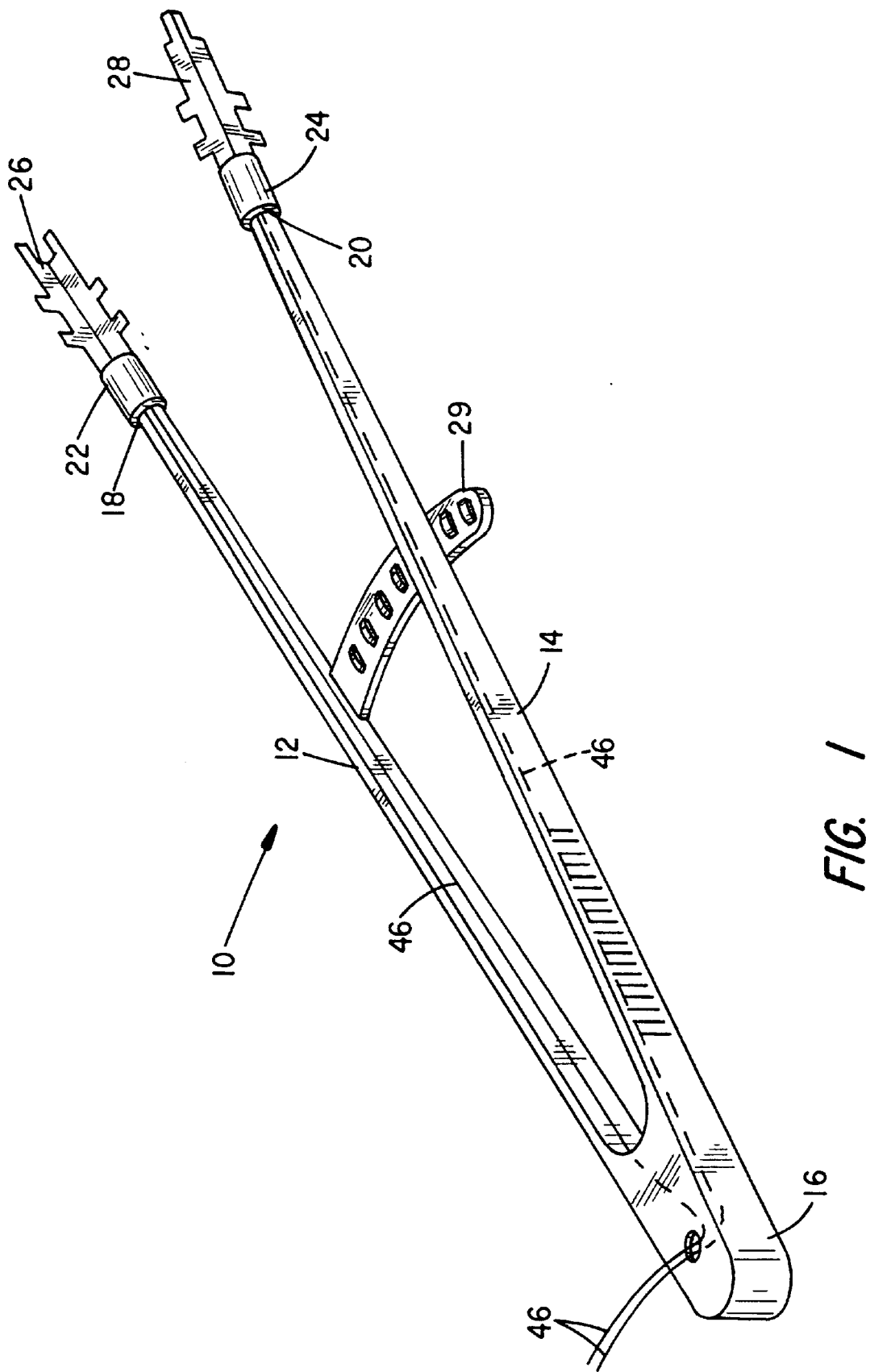
FIG. 1 illustrates an electrosurgical forceps intended for open procedures and having the improved jaw configuration in accordance with the present invention.

Referring first to FIG. 1, there is indicated generally by numeral 10 a forceps-type instrument designed for use in open surgical procedures. It includes a pair of resilient bifurcated legs 12 and 14 that are joined together at their proximal ends, as at 16, thereby forming a handle structure. Affixed to the distal ends 18–20 of the bifurcated legs 12 and 14 are insulating (ceramic) spacers 22 and 24. The forceps jaws 26 and 28 are affixed to the spacers 22 and 24 to project longitudinally from the distal end thereof. A locking detent 29 of conventional make-up is affixed to the cooperating legs 12 and 14 allowing the gap between the forceps jaws to be set.

Figure 2:
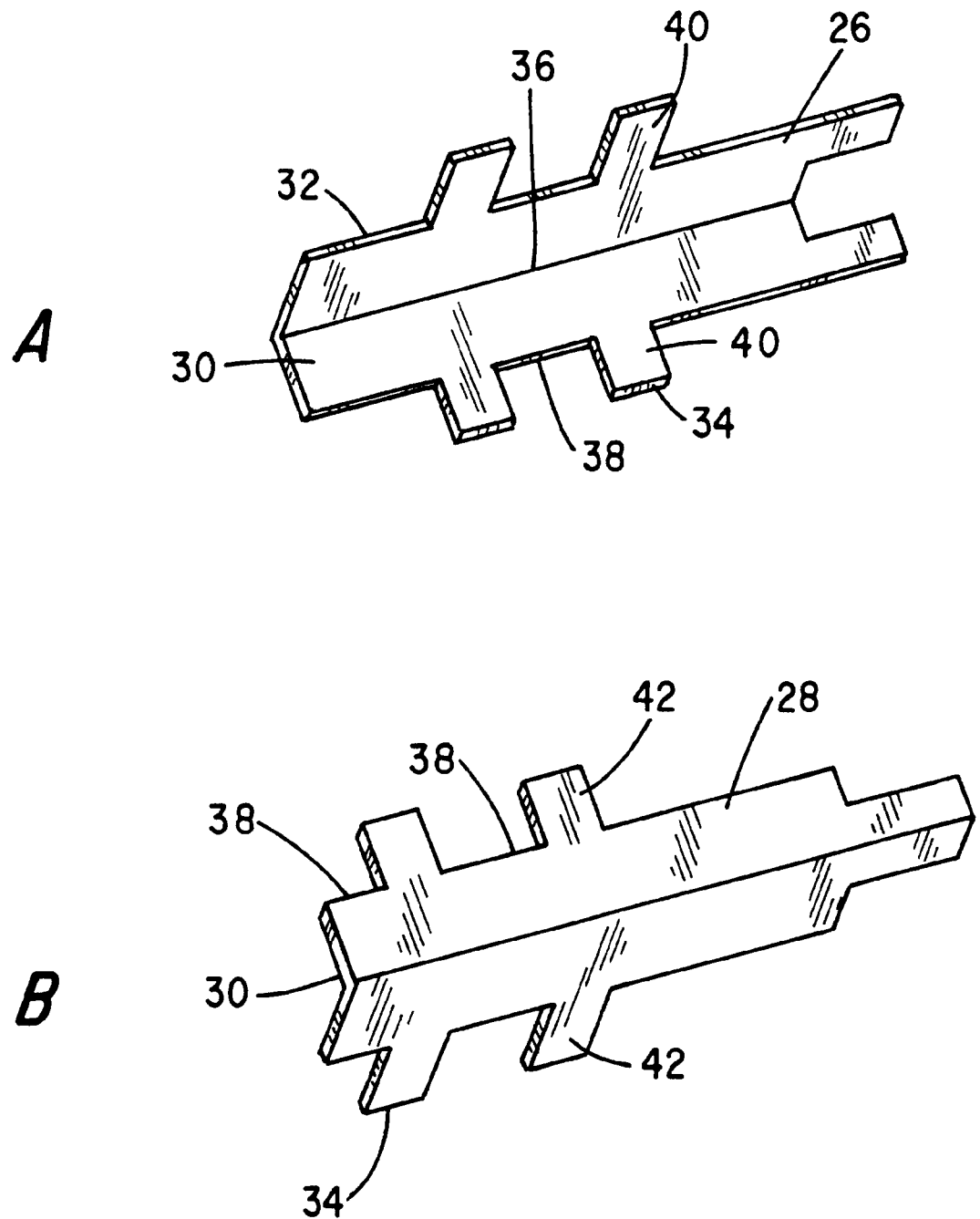
FIG. 2 is an enlarged, exploded, perspective view of the forceps jaws shown in FIG. 1.

As can best be seen in the exploded perspective view of FIG. 2, the jaws 26 and 28 of the forceps each comprise a conductive metal sheet 30 having first and second side edges 32 and 34 and each being folded at a predetermined angle, preferably in a range of from about 115° to 140°, along a longitudinal axis 36 that is preferably but not necessarily midway between the first and second side edges 32 and 34. The side edges of the sheets 30 have a plurality of spaced, inwardly extending notches, as at 38, that define a plurality of rectangular tabs 40 on jaw member 26 and 42 on jaw member 28. The tabs on the side edges of each of the jaw members are non-coplanar.

Figure 3:
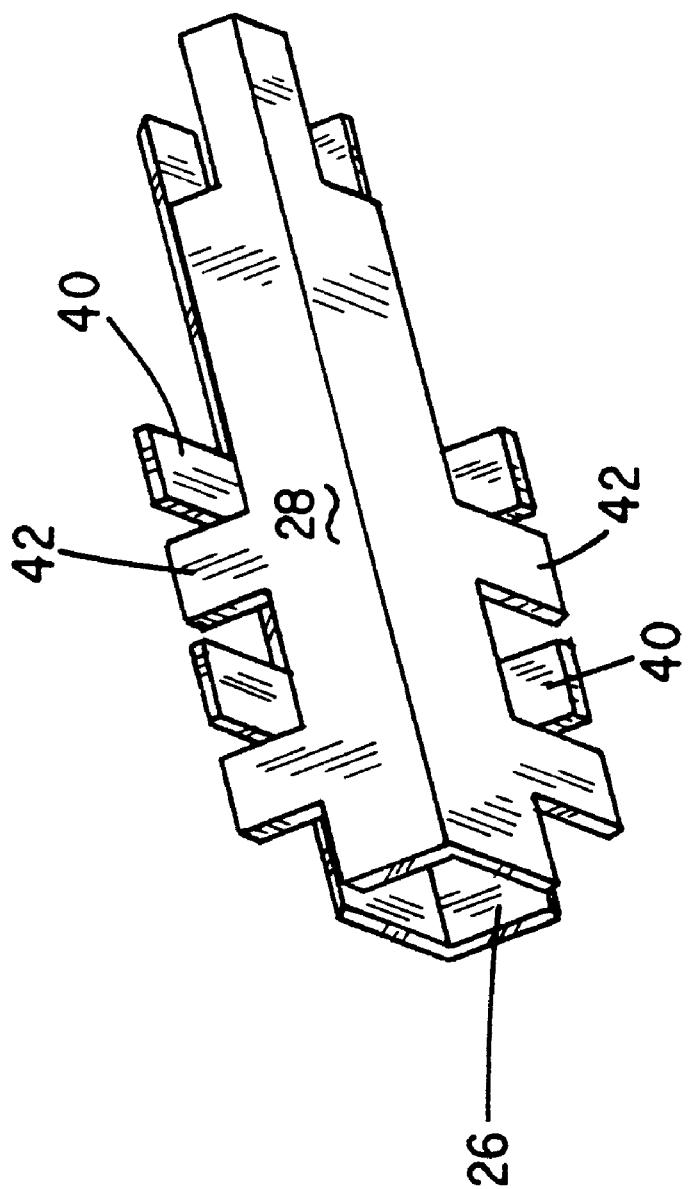
FIG. 3 is a further perspective view of the forceps jaws when closed relative to one another.

With reference to FIG. 1, the jaw members 26 and 28 are supported on the forceps legs 12 and 14 such that when the pair of jaws are closed and latched relative to one another, the plurality of tabs on the side edges of one of the pair of jaws fit into the notches on the side edges of the other of the pair of jaws and without the jaws and tabs contacting one another, as is more clearly illustrated in the perspective partial view of FIG. 3. In particular, the spacers 20 and 22 are of an outer diameter such that they come together and touch at a point where the jaws 26 and 28 are not physically touching on another, but the tabs have their exposed free ends aligned collinearly. That is, the exposed free ends of the tabs 40 on the jaw member 26 are collinear with the exposed free ends of the tabs 42 on the jaw 28. As such, when an RF voltage is applied, via conductors 46, to the jaws 26 and 28, current flows in the tissue bridging adjacent tabs as the free ends thereof are drawn, scalpel-like, across the tissue to be cut. The RF current density is greatest at the sharply angled edges of the adjacent tabs. It does not matter which of the two jaws happens to be the active electrode at any given time in that the associated return electrode tracks directly behind in the same path as the active electrode as a cut is being made. As such, there is no frictional drag between the return or inactive electrode and adjacent tissue as there is in prior art devices.

Figure 4:
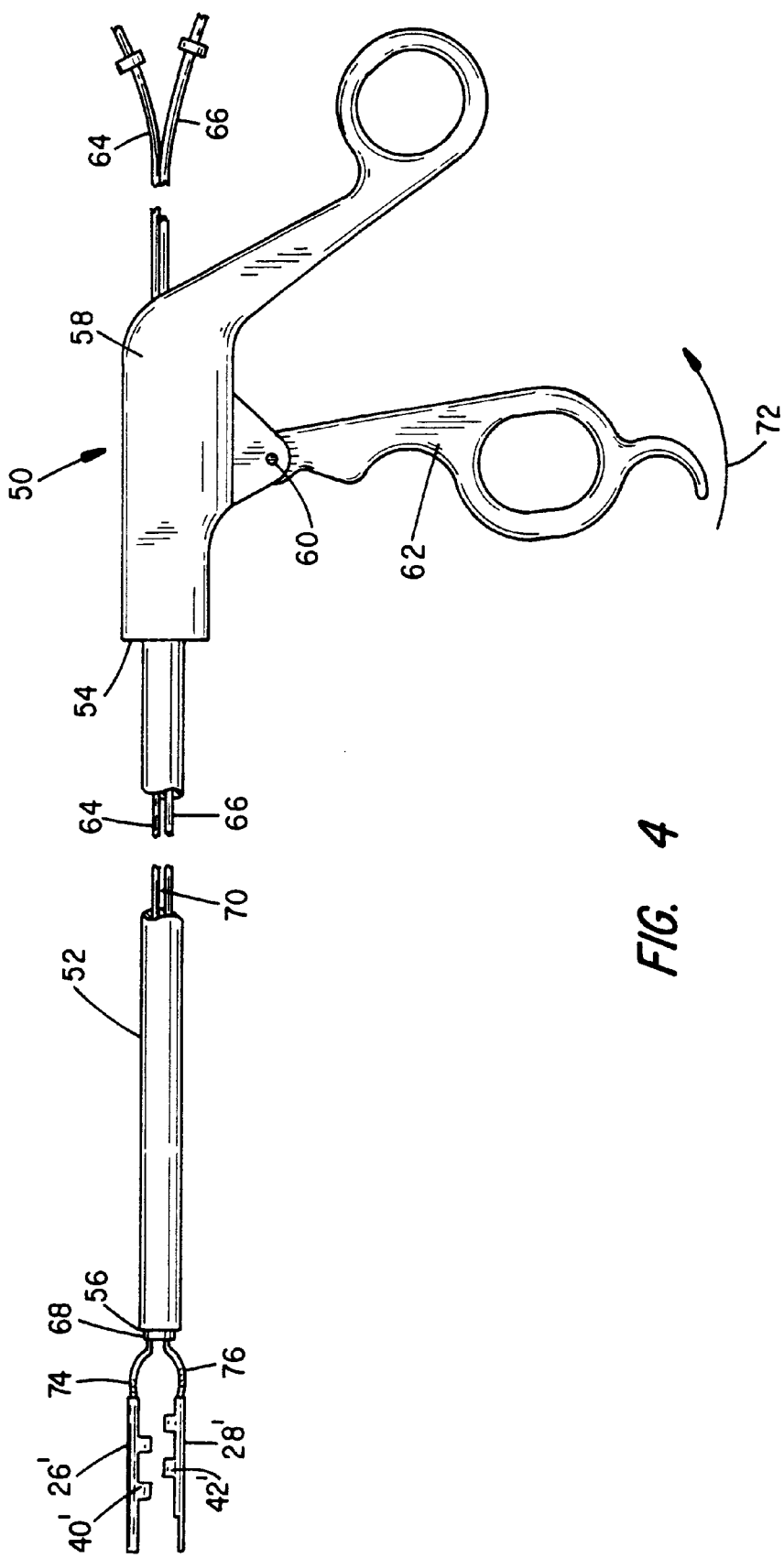
FIG. 4 illustrates forceps designed for endoscopic uses and embodying the improved jaw configuration of the present invention for facilitating electrosurgical cutting.

FIG. 4 shows the principles of the present invention applied to an endoscopic electrosurgical cutting/coagulating forceps instrument. The instrument is indicated generally by numeral 50 and includes an elongated tubular barrel 52 having a proximal end 54 and a distal end of 56. Affixed to the proximal of the tubular barrel is a stationary handle member 58 and pivotally secured thereto at a pivot point 60 is a movable handle member 62.

Conductors 64 and 66 extend through the stationary handle portion 58 and through a lumen of the tubular barrel 52 to the distal end 56 of the instrument where they join to forceps jaws 26' and 28'. The jaws are designed to fit within longitudinal bores of an insulating cylindrical stem 68 that is connected by an actuator rod 70 to the movable handle member 62. Movement of the handle member 62 in the direction of the arrow 72 functions to draw the insulating cylindrical stem 68 further into the distal end 56 of the barrel 52 at which point the distal end of the barrel 52 rides against arcuate ramp segments 74 and 76 of the jaws 26' and 28', causing the jaws to close relative to one another.

As with the earlier embodiment, the tabs 40' and 42' on the forceps jaws become interleaved in the manner illustrated in FIG. 3, allowing the free exposed ends of the tabs to become aligned and to function as an electrosurgical scalpel blade during cutting operations.

Figure 5:
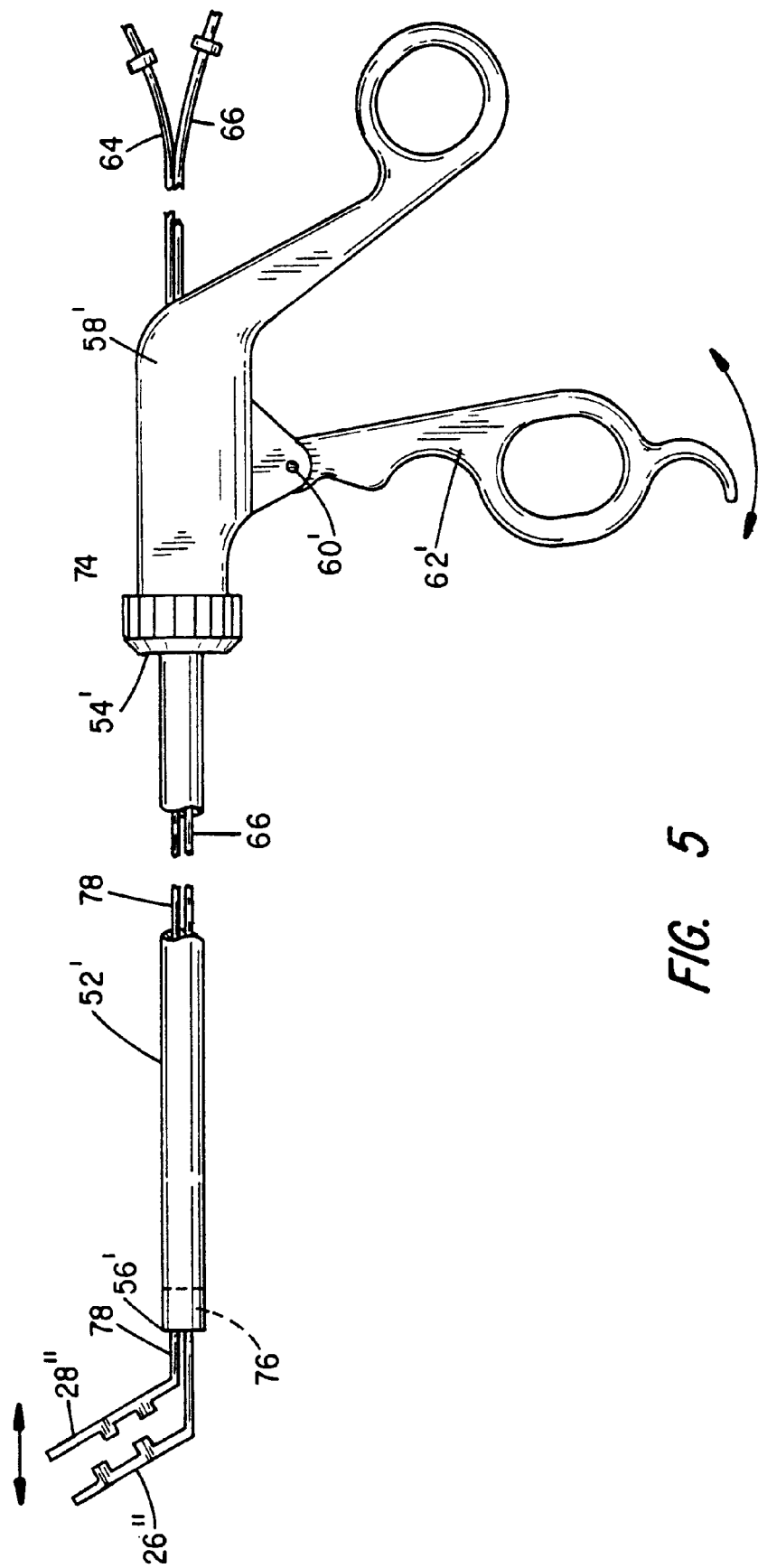
FIG. 5 is a side elevation of an endoscopic version of an electrosurgical cutting/coagulating forceps in accordance with an alternative embodiment of the invention.

FIG. 5 illustrates an alternative embodiment of a cutting/coagulating forceps incorporating the present invention. The instrument is shown as being designed for endoscopic surgical applications and, as such, includes an elongated barrel 52' dimensioned to fit through the working lumen of a viewing endoscope (not shown). Affixed to the proximal end 54' of the tubular barrel 52' is a rotatable knob 74 which facilitates rotation of the barrel 52' and the effectors 26" and 28" project out from the distal end 56' of the tubular barrel. The manner in which the tubular barrel is rotatably mounted to the fixed portion 58' of the handle is fully disclosed in the Rydell et al. U.S. Pat. No. 5,258,006 assigned to applicant's assignee.

The effector 26" is affixed to an insulating disk 76 that fits into the distal end 56" of the tubular barrel 52' and, thus, the effector 26" is relatively stationary with respect to the tubular barrel 52'. The insulating disk 76 includes a bore therethrough through which a conductive push rod 78 passes with a sliding fit. The effector 28" is attached to the push rod 78 which, in turn, is appropriately coupled to the movable handle member 62' such that closure of the handle 62' relative to the stationary handle member causes the effector 28" to move toward the stationary effector 26".

In each instance, the effectors 26" and 28" are configured in accordance with the configuration illustrated in FIGS. 2 and 3. That is, each of the effectors 26" and 28" comprises a conductive metal member having first and second side edges with the sheet being folded or otherwise formed at a predetermined angle along a longitudinal axis approximately midway between the first and second side edges. The side edges on each of the effectors have a plurality of regularly spaced, inwardly extending notches defining a plurality of tabs. The effector 26" remains stationary relative to the handle while the effector 28" can be moved toward and away from effector 26" by manipulating the handle 62'. When the effectors 26" and 28" are fully closed relative to one another, the plurality of tabs on the side edges on one of the effectors fits into the notches on the side edges of the other effector without their physically touching one another, but with the exposed end edges of the tabs on the two effectors collinearly aligned. The effectors 26" and 28" are shown as being bent at a predetermined angle to the longitudinal axis of the barrel. This angle preferably is about 45°. When so configured, the instrument of FIG. 5 finds practical use in harvesting the mammary artery of a patient during the course of a coronary bypass procedure.

To further reduce any frictional drag when the effectors are closed relative to one another and the instrument is being used as an electrosurgical scalpel, it has been found expedient to coat or otherwise treat the effectors with a lubricious material, such as Teflon or silicone dioxide. If such a coating is used, the free edges of the tabs on each of the effectors would be appropriate burnished to remove insulating material from the electrode surfaces.

With no limitation intended, the forceps jaws may be fabricated from a stainless steel sheet having a thickness of about 0.20 inch and may be approximately ½ inches in length. The tabs 40 and 42 may be 0.050 inch in width and 0.060 inch in depth. The overall width dimension of the sheets 30 may be about 0.195 inch.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. In a bipolar electrosurgical instrument of the type including a handle member for supporting a pair of effectors and having a means for selectively applying a voltage across said pair of effectors, the improvement comprising:

said pair of effectors each being a conductive metal having first and second side edges and being formed at an angle less than 180° along a longitudinal axis between the first and second side edges, the side edges of the pair of effectors having a plurality of spaced, inwardly extending notches defining a plurality of tabs, the pair of effectors being supported by the handle member with the plurality of tabs on the side edges of one of the pair of effectors fit into the notches on the side edges of the other of the pair of effectors without the effectors contacting one another and with exposed end edges of the tabs on the first of the pair of effectors collinear with exposed end edges of the tabs on the side edges of the second of the pair of effectors.

2. The electrosurgical instrument as in claim 1 wherein said pair of effectors are forceps jaws, at least one of which is relatively moveable with respect to the other.

3. The electrosurgical instrument as in claim 2 and further including means for releasably locking the pair of forceps jaws with a predetermined spacing therebetween.

4. In a bipolar electrosurgical forceps for grasping and cutting tissue of the type having a handle member, a pair of forceps jaws operatively coupled to the handle member; means for opening and closing said pair of jaws relative to one another and means for selectively applying a voltage between said pair of forceps jaws, the improvement comprising:

said pair of jaws each comprising a conductive metal member of predetermined thickness and length dimension and having first and second parallel, spaced-apart side edges, each with a plurality of inwardly extending, spaced-apart notches defining a plurality of tabs, the metal members being bent such that said plurality of tabs on the first side edge is non-coplanar with the plurality of tabs on the second side edge, said pair of jaws being supported by the handle member such that when the pair of jaws are closed relative to one another, the plurality of tabs on the first and second side edges of one of the pair of jaws reside in the plurality of notches in the first and second side edges of the other of the pair of jaws and with the pair of jaws out of electrical contact with one another.

5. The electrosurgical forceps of claim 4 wherein the metal member is a stainless steel sheet and the predetermined thickness dimension is about 0.020 inch.

6. The electrosurgical forceps of claim 4 wherein the plurality of tabs on each of the pair of jaws have a free end edge and the free end edges of the tabs on the first side edge of one of the pair of jaws are collinear with the free end edges of the tabs on the first side edge of the other of the pair of jaws when the pair of jaws are closed relative to one another.

7. The electrosurgical forceps of claim 6 wherein the plurality of notches are about 0.075 inch wide and about 0.060 inch deep.

8. The electrosurgical forceps of claim 7 wherein said plurality of tabs are about 0.050 inch wide and about 0.060 inch long.

9. The electrosurgical forceps as in claim 4 wherein the handle member comprises an elongated tubular barrel having a proximal end, a distal end and a lumen extending therebetween with one of the pair of jaws immovably affixed at the distal end of the tubular barrel and the other of the pair of jaws displaceable relative to the one of the pair of jaws; and means disposed at the proximal end of the barrel for displacing the other of the pair of jaws.

10. The electrosurgical forceps as in claim 9 wherein the pair of jaws are supported by the handle member at a predetermined angle to a longitudinal axis of the barrel.

11. In a bipolar electrosurgical instrument of the type including a handle member for supporting a pair of effectors and having a means for selectively applying a voltage across said pair of effectors, the improvement comprising:

said pair of effectors each being a conductive metal having first and second side edges, each side edge having at least one laterally projecting tab bent at an angle to a plane defining said side edges, the pair of effectors being supported by the handle member with the at least one tab on the first and second side edges of one of the pair of effectors longitudinally offset from the at least one tab on the first and second edges of the other of the pair of effectors without the effectors contacting one another and with exposed end edges of the at least one tab on the first and second side edges of the one of the pair of effectors collinear with the exposed end edges of the at least one tab on the first and second side edges of the other of the pair of effectors.

12. The electrosurgical instrument as in claim 11 wherein said pair of effectors are forceps jaws, at least one of which is relatively movable with respect to the other.

13. The electrosurgical instrument as in claim 12 and further including means for releasibly locking the pair of forceps jaws with a predetermined spacing therebetween.

14. The electrosurgical instrument as in claim 11 wherein the handle member comprises an elongated tubular barrel having a proximal end, a distal end and a lumen extending therebetween with one of the pair of effectors immovably affixed at the distal end of the tubular barrel and the other of the pair of effectors displaceable relative to the one of the pair of effectors; and means disposed at the proximal end of the barrel for displacing the other of the pair of effectors.

15. The electrosurgical instrument as in claim 14 wherein the pair of effectors are supported by the handle member at a predetermined angle to the longitudinal axis of the barrel.

* * * * *